US008888287B2

(12) United States Patent
Yahav

(10) Patent No.: US 8,888,287 B2
(45) Date of Patent: *Nov. 18, 2014

(54) HUMAN-COMPUTER INTERFACE SYSTEM HAVING A 3D GAZE TRACKER

(71) Applicant: Microsoft Corporation, Redmond, WA (US)

(72) Inventor: Giora Yahav, Haifa (IL)

(73) Assignee: Microsoft Corporation, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/783,417

(22) Filed: Mar. 4, 2013

(65) Prior Publication Data

US 2013/0178287 A1 Jul. 11, 2013

Related U.S. Application Data

(63) Continuation-in-part of application No. 12/965,948, filed on Dec. 13, 2010, now Pat. No. 8,408,706.

(51) Int. Cl.
*A61B 3/14* (2006.01)
*A61B 3/00* (2006.01)

(52) U.S. Cl.
USPC ............................ 351/210; 351/209; 351/246

(58) Field of Classification Search
USPC .................................................. 351/200–246
See application file for complete search history.

(56) References Cited

U.S. PATENT DOCUMENTS

| 5,471,542 | A | * | 11/1995 | Ragland ........................ 382/128 |
|---|---|---|---|---|
| 6,578,962 | B1 | | 6/2003 | Amir et al. |
| 7,561,143 | B1 | | 7/2009 | Milekic |
| 8,032,842 | B2 | | 10/2011 | Kwon et al. |
| 8,154,583 | B2 | | 4/2012 | Kurtz et al. |
| 8,205,165 | B2 | | 6/2012 | Dal Lago |
| 8,254,633 | B1 | | 8/2012 | Moon et al. |
| 2009/0252423 | A1 | | 10/2009 | Zhu et al. |
| 2009/0290753 | A1 | | 11/2009 | Liu et al. |
| 2011/0043644 | A1 | * | 2/2011 | Munger et al. ............. 348/207.1 |
| 2011/0141011 | A1 | | 6/2011 | Lashina et al. |
| 2011/0170067 | A1 | | 7/2011 | Sato et al. |
| 2012/0146891 | A1 | | 6/2012 | Kalinli |
| 2013/0083976 | A1 | * | 4/2013 | Ragland ........................ 382/117 |

FOREIGN PATENT DOCUMENTS

WO    0209025 A1    1/2002

OTHER PUBLICATIONS

Ki, et al., "3d Gaze Estimation and Interaction", retrieved at <<http://ieeexplore.ieee.org/stamp/stamp.jsp?tp=&arnumber=4547886>> In 3DTV Conference: The True Vision—Capture, Transmission and Display of 3D Video, May 28, 2008, pp. 4.

Ki, et al., "3D Gaze Tracking and Analysis for Attentive Human Computer Interaction", retrieved at <<http://ieeexplore.ieee.org/stamp/stamp.jsp?tp=&arnumber=4524177>> In Proceedings of Frontiers in the Convergence of Bioscience and Information Technologies, Oct. 11, 2007, pp. 5.

Chinese Office Action: 201110436594.7, dated Nov. 15, 2013.

* cited by examiner

*Primary Examiner* — Mohammed Hasan
(74) *Attorney, Agent, or Firm* — Gregg Wisdom; Judy Yee; Micky Minhas

(57) ABSTRACT

An apparatus for interfacing a person with a computer, the apparatus comprising a gaze tracker having a 3D camera and a picture camera that image the person and a controller that processes images acquired by the cameras to determine a gaze direction and point of regard of the person.

20 Claims, 8 Drawing Sheets

HUMAN-COMPUTER INTERFACE SYSTEM HAVING A 3D GAZE TRACKER

RELATED APPLICATIONS

The present application is a continuation-in-part of U.S. patent application Ser. No. 12/965,948 filed Dec. 13, 2010 Now U.S. Pat. No. 8,408,706 B2, which is incorporated herein reference.

TECHNICAL FIELD

Embodiments of the invention relate to methods and apparatus for tracking a person's gaze and "point of regard" (POR) to which the gaze is attended, and systems that use the methods and apparatus to interface a person with a computer.

BACKGROUND

Various types of eye tracking, or gaze tracking, systems for determining a direction of a person's gaze and what the person is looking at, are known in the art. The systems are used, by way of example, for ergonomic and medical research, diagnostics, and interfacing a person with a computer, or a computer generated artificial environment.

Generally, the systems operate to determine a location for the person's pupil, and a gaze direction along which the person is looking, which is defined as a direction of a "gaze vector" that extends out from the eye along a line from a center of rotation of the eye through the center of the located pupil. A location of the eye in three-dimensional (3D) space is determined and used to determine coordinates of a region of space through which the gaze vector passes. The determined coordinates of the region, hereinafter referred to as an "origin" of the vector, locate the gaze vector in space. Given the direction and origin of the gaze vector, its intersection with a region or object in the person's environment is identified to determine what the person is looking at, which, presumably, is a point regard (POR) to which the person's attention is directed.

Hereinafter, a POR, is assumed to be coincident with an intersection of a person's direction of gaze and an object or region in the person's environment, and is used to refer to the intersection, object, or region. A gaze tracking system, hereinafter referred to as a "gaze tracker", provides both a direction and an origin for a person's gaze vector, and optionally a POR, for the person.

Intrusive and non-intrusive methods and gaze trackers exist for determining a direction for a gaze vector. In some intrusive gaze trackers a person wears special contact lenses comprising induction micro-coils that move with the eye and pupil. A high frequency electromagnetic field is used to track orientation of the micro-coils and thereby the person's eyes and direction of gaze. In some intrusive gaze trackers, a person is fitted with electrodes that sense changes in orientation of a dipole electric field that the eye generates to determine direction of gaze.

Non-intrusive gaze trackers and tracking methods often image reflections, referred to as "Purkinje reflections", of light from surfaces of different structures of the eye and process images of the reflections to determine their relative motion, and therefrom changes in direction of a person's gaze. The changes in gaze direction are referenced to a reference gaze direction to determine the person's gaze direction. First, second, third, and fourth Purkinje reflections refer respectively to reflections from the front surface of the cornea, from the back surface of the cornea, the front surface of the lens and the back surface of the lens.

For a given stationary source of light, reflections from the front surface of the cornea, the first Purkinje reflection, are strongest and are conventionally referred to as "glints". Locations of images of glints are relatively independent of direction of gaze for moderate eye rotations (eye rotations up to about ±15°) and a fixed position of the head. Locations of images of glints are typically used to reference motion of images of features of the eye or of other Purkinje reflections to determine changes in a person's gaze direction.

In many non-intrusive gaze trackers, changes in location of an image of the pupil relative to an image of a glint are used to determine gaze direction. In some non-intrusive gaze trackers, reflections of light from the retina, which are not usually classified as a Purkinje reflections are used to image the pupil and track eye motion and gaze direction. The retina acts like a retro reflector and light that enters the pupil and is reflected by the retina exits the pupil along a direction that it entered the eye and backlights the pupil. The retinal backlighting of the pupil produces the familiar "bright eye", or "red eye" effect, frequently seen in images of people's faces acquired with a flash. Bright eye pupil images of a person are acquired by a camera using light sources that illuminate the person's face from a direction substantially coincident with the camera optic axis. Locations of the bright eye pupil in the images are tracked relative to locations of glints in the images to determine the person's gaze direction. Bright eye pupil images are not produced by off axis light sources, and for off axis light sources, an imaged pupil appears dark. In many non-intrusive gaze trackers, locations of "dark pupil images" are compared to locations of images of glints to determine direction of gaze.

For many applications of a gaze tracker, a person's head is required to be stabilized relative to components of the gaze tracker so that it can provide acceptably accurate determinations of a direction and an origin for a gaze vector, and therefrom a POR for the person. For some gaze trackers, the person's head is stabilized by a static support, such as a chin rest often used in ophthalmic examinations, or a bite bar, to fix the head and eyes relative to components of the gaze trackers.

For applications such as interfacing a person with a virtual or augmented reality, it is advantageous for the person to be able to freely move his or her head and for these applications, a person typically wears a headgear, such as a helmet or goggles, that comprises gaze tracker components. The headgear holds the gaze tracker components in substantially fixed locations relative to the person's head and provides fixed, known, distances and orientations of the eye relative to the components. The known distances and orientations facilitate determining gaze vector directions and origins for the person relative to the headgear. Gaze vector directions and origins relative to the real world, a virtual or augmented reality, are determined from the gaze directions and origins relative to the headgear, and orientation of the headgear in the real world. Orientation of the headgear is determined using any of various optical, electromagnetic or mechanical position and orientation sensor systems.

Some gaze trackers provide directions and origins of gaze vectors and PORs for a person without recourse to a worn headgear. However, these gaze trackers generally operate for head positions restricted to a relatively small range of distances between about 50 cm (centimeter) and about 80 cm from the gaze trackers.

SUMMARY

An embodiment of the invention provides a three-dimensional (3D) gaze tracker and a system that uses the 3D gaze tracker to interface a person with a computer. The 3D gaze tracker determines gaze vectors for a person who is substantially unencumbered by gaze tracking headgear and enjoying freedom of motion in a field of view (FOV) of the gaze tracker having a depth of field that extends to a relatively large distance from the tracker. Optionally, the gaze tracker determines a POR for gaze vectors that it determines. In an embodiment of the invention, the computer may generate images on a video display to interact with the person and the 3D gaze tracker, or a processor that receives data defining the POR determined by the 3D gaze tracker, generates an icon indicating location of the POR on the video display.

In an embodiment of the invention, the 3D gaze tracker comprises a 3D camera, which acquires range images of the person that provide 3D spatial coordinates for features of the person's face and/or head, and a camera, hereinafter also a "picture camera", which acquires contrast images, hereinafter "pictures", of the features. A processor processes the contrast and range images to distinguish the person's eyes and features of the eyes, for example, an eye glint a bright or dark pupil, and features of the face or head, such as the nose, chin or forehead, and determines 3D spatial coordinates for the features. The processor provides directions and origins for gaze vectors for the person, and optionally PORs associated with the gaze vectors, responsive to the distinguished features, and their 3D spatial coordinates.

Optionally, the 3D camera comprises a time of flight (TOF) 3D camera configured to provide range images in a FOV that extends to a distance between at least 1 m (meter) and 3 m from the gaze tracker. Optionally, the FOV extends from a distance equal to about 30 cm from the gaze tracker.

In the discussion, unless otherwise stated, adverbs such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

In the detailed description below aspects of embodiments of the invention are discussed with respect to a 3D gaze tracker schematically shown in FIGS. 1A and 1B, which comprises a TOF 3D camera, and a picture camera, in accordance with an embodiment of the invention. Aspects of determining gaze directions responsive to images of eye glints and pupils acquired by the 3D gaze tracker, in accordance with an embodiment of the invention, are discussed with reference to FIGS. 2A-2C. Effects of head orientation on determining gaze directions, and aspects of determining head orientations and gaze directions by the 3D gaze tracker in accordance with an embodiment of the invention are illustrated and discussed with reference to FIGS. 3A-3C. A variation of a 3D gaze tracker that tracks a person with a cone of light to provide enhanced illumination of the person, in accordance with an embodiment of the invention, is discussed with reference to FIG. 4. Determinations of gaze vector origins using range images acquired by a 3D gaze tracker in accordance with an embodiment of the invention are discussed with reference to FIG. 5. FIG. 6 schematically shows an embodiment of a 3D gaze tracker comprising a stereoscopic 3D imager that determines distances by triangulation.

Figure 1A:
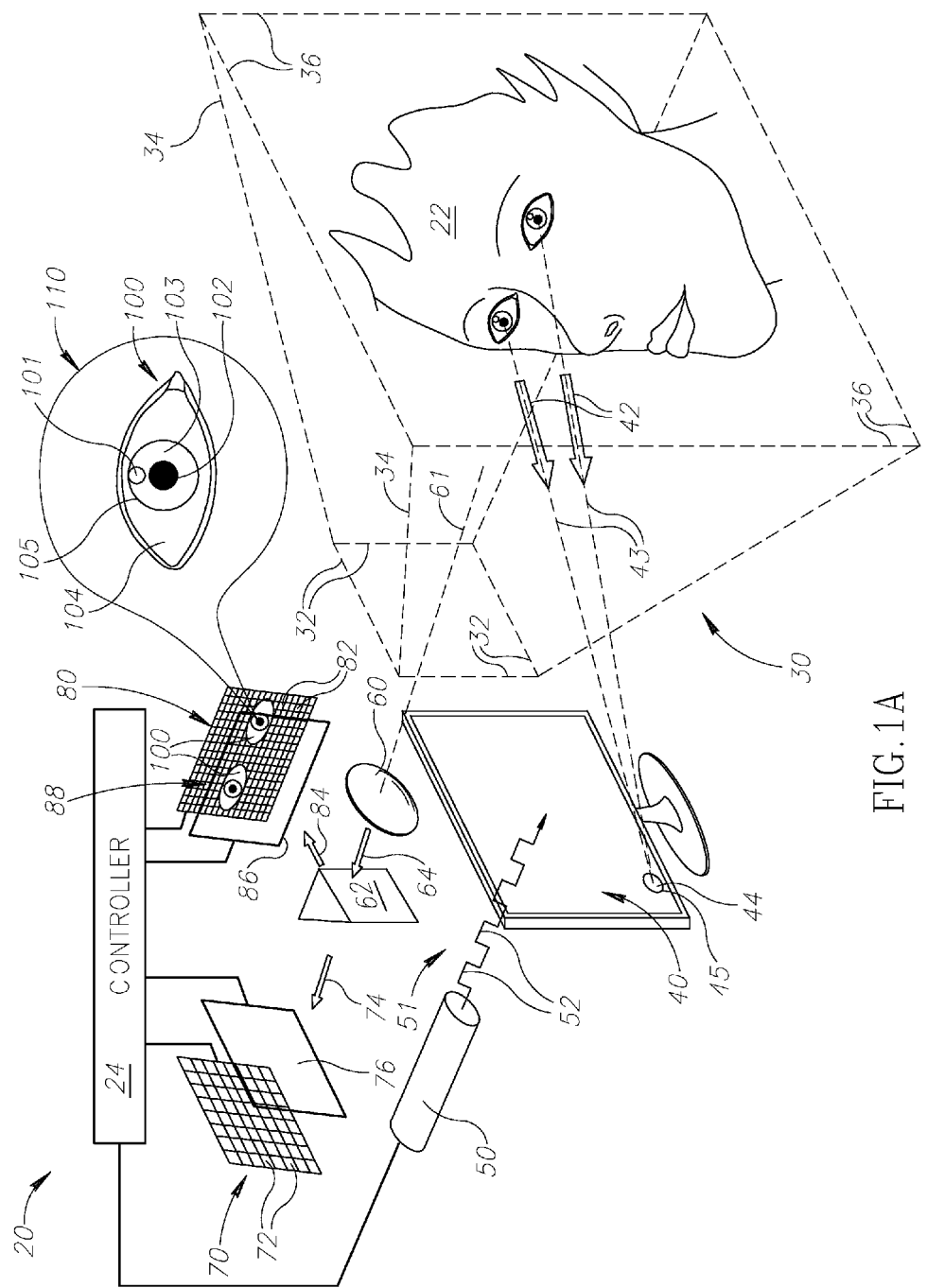
FIG. 1A schematically shows a 3D gaze tracker comprising a TOF 3D camera determining gaze vectors and a POR for a person, in accordance with an embodiment of the invention.

FIG. 1A schematically shows a 3D gaze tracker 20 imaging a person 22 whose head is located within a field of view (FOV) 30 of the 3D gaze tracker, in accordance with an embodiment of the invention. The gaze tracker is tracking the person's gaze by determining gaze vectors and PORs for the person as he or she moves around, and engages in activities, in the FOV. A dashed line 61 represents an optical axis of the 3D gaze tracker, and dashed lines 32, 34, and 36, outline a frustum delimiting a volume of FOV 30. The FOV has a depth of field extending from 3D gaze tracker 20 having a minimum, lower bound range schematically indicated by location of a plane defined by dashed lines 32, and a maximum, upper bound range schematically indicated by location of a plane defined by dashed lines 36.

In some embodiments of the invention, the lower bound range is equal to or greater than about 30 cm. Optionally, the lower bound range is equal to or greater than about 50 cm. In some embodiments of the invention, the upper bound range is greater than or equal to about 1 m. Optionally, the upper bound range is equal to or greater than about 2 m. In some embodiments of the invention, the upper bound range is equal to about 3 m.

A view angle of 3D gaze tracker 20 is a largest possible angle between lines that lie in FOV 30 and a plane through optical axis 61. Horizontal and vertical view angles are view angles for horizontal (parallel to the ground) and vertical (perpendicular to the ground) planes respectively that contain optical axis 61. In some embodiments of the invention, at least one of the horizontal and vertical view angles is equal to or greater than about 45°. Optionally, at least one of the view angles is equal to or greater than 90°. In some embodiments of the invention, at least one of the view angles is equal to about 120° or 150°.

By way of example, 3D gaze tracker 20 is assumed to be tracking the gaze of person 22 to interface the person with a computer (not shown) via a video display 40. Video display 40 may be any of various video displays, such as by way of non-limiting example, a desk top computer screen, a video game console screen, a tablet screen, or a smartphone screen. The computer, also referred to as the "video display computer", may be any processing device or system, such as by way of non-limiting example, a gaming console configured to support online video gaming, a laptop, smartphone, or tablet, that uses video display 40 to interface with person 22.

Block arrows 42 in FIG. 1A schematically represent gaze vectors for person 22, and dashed lines 43 indicate their directions as converging to a POR 44 at the lower left corner of video display 40. A controller 24 controls 3D gaze tracker 20 and may be interfaced with the video display computer by a suitable application programming interface (API) so that information generated by the 3D gaze tracker is applicable to images displayed on video display 40 and may be used to modify the images. Modifying the displayed images comprises effecting any change to the displayed images, and comprises by way of example, making a change to the images themselves or adding information to the images.

It is noted that whereas in the above description controller 24 may be understood to be separate from the video display computer, controller 24 may be integrated with, comprise, or be comprised in the video display computer and may be implemented using any combination of hardware or software components. Controller 24, as well as the video display computer may for example, and without limitation, comprise an application specific integrated circuit (ASIC), a field programmable gate array (FPGA) or a system on a chip that may store and execute an instruction set that provides a functionality of 3D gaze tracker 20 or the video display computer. Controller 24 may comprise a general purpose processor having access to, or including a computer readable memory storing an executable instruction set which the processor executes to provide a functionality of 3D gaze tracker 20 or the video display computer. Controller 24 may be configured as a distributed system, optionally implemented in the cloud, having various functionalities that communicate with each other to cooperate in performing tasks of 3D gaze tracker 20.

In an embodiment of the invention, controller 24 generates information that the API uses to indicate on video display 40 a location of POR 44. Optionally, controller 24 provides information that defines a region of uncertainty (ROU) for the location of POR 44 determined by 3D gaze tracker 20. For example, location of POR 44 may be visibly indicated on video display 40 by a suitable "POR icon", which as schematically shown in FIG. 1A may be a circle 45. Diameter of circle 45 may indicate accuracy, a ROU, with which the 3D gaze tracker 20 determines location of POR 44.

The location of POR icon 45 provides visual feedback for person 22 which the person may use to adjust a location for his or her POR in response to displays generated on video display 40. For example, 3D gaze tracker 20 may be used to enable person 22 to interact with a video game presented on video display 40 by the video display computer. As an illustrative non-limiting example, the video game might be an aerial dogfight video game schematically shown in FIG. 1B, in which person 22 attempts to follow a maneuvering enemy fighter 91 with her eyes to center her POR 44 on the fighter. When person 22 sees that her POR 44 as indicated by circle 45 is centered on enemy fighter 91 she may operate, optionally, a joystick (not shown) to release an air to air missile (not shown) or fire a canon (not shown) to destroy the enemy fighter.

Figure 1B:
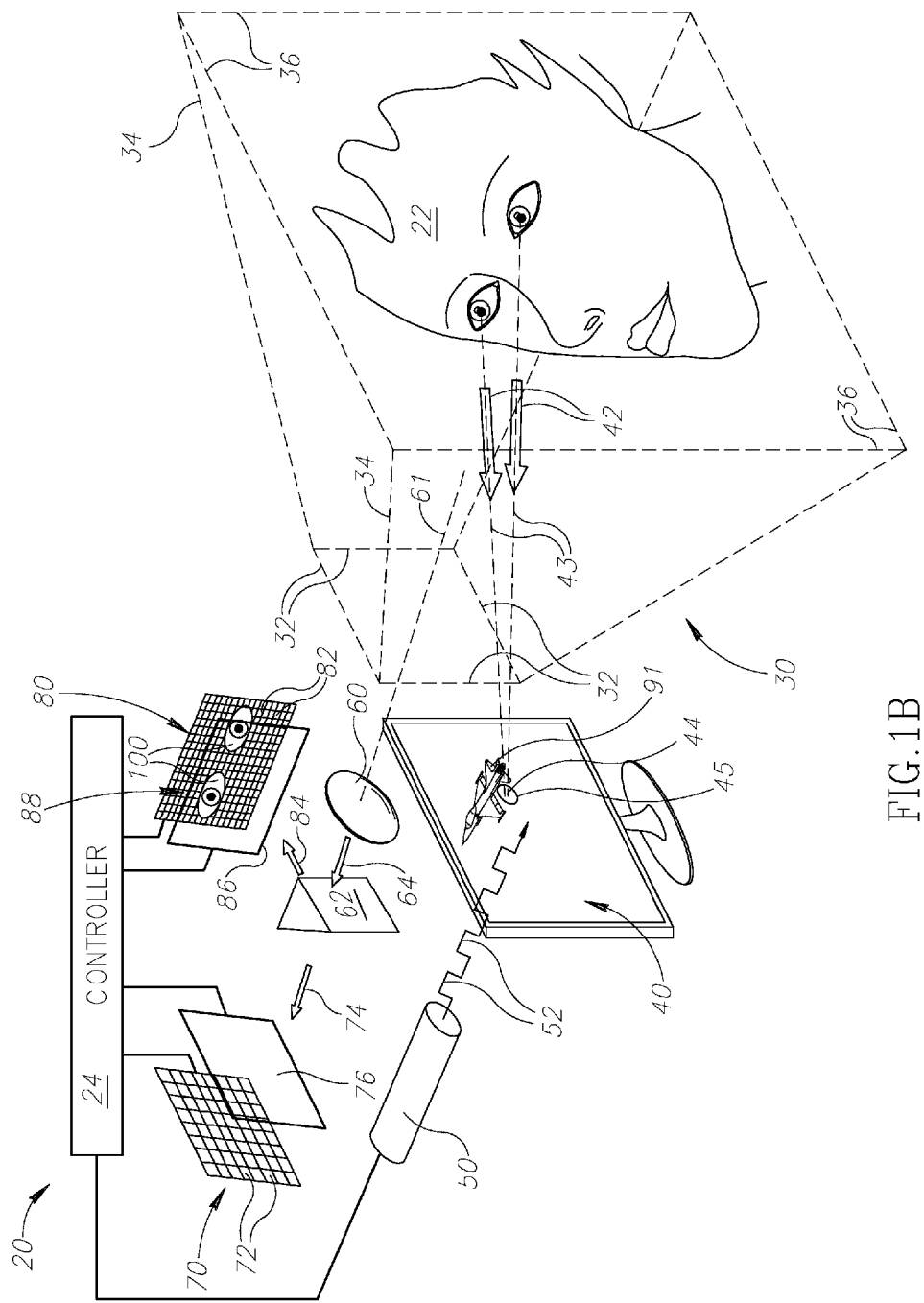
FIG. 1B schematically shows the 3D gaze tracker shown in FIG. 1A being used in a video game, in accordance with an embodiment of the invention.

The 3D gaze tracker optionally comprises a light source 50 controllable by controller 24 to radiate a train 51 of light pulses, schematically represented by square "pulses" labeled with a numeral 52, to illuminate objects and people in FOV 30, and by way of example in FIGS. 1A and 1B, person 22. Numeral 52 is also used to refer to the light pulses. Whereas light pulses 52 may comprise light from any portion of the spectrum provided by a suitable light emitting diode (LED) and/or laser, usually the light pulses are vision safe, near infrared (NIR) light pulses.

An optical system, represented by a lens 60 having an optical axis that coincides with optical axis 61, comprised in 3D gaze tracker 20 collects light from light pulses 52 that is reflected back to the 3D gaze tracker by features of person 22, and directs the collected light to a beam splitter 62. Light that beam splitter 62 receives from lens 60 is schematically represented by a block arrow 64, and the numeral 64 is used to reference the light.

Beam splitter 62 directs, optionally about one-half, of the light it receives from lens 60 to a photosensor 70, hereinafter also referred to as a "range photosensor 70", having light sensitive pixels 72 (FIG. 1A). Light that beam splitter 62 directs to range photosensor 70 is represented by a block arrow 74 and the numeral 74 is used to reference the light. Photosensor 70 is shuttered open or closed to respectively enable it to register light 74 or prevent it from registering the light. Optionally, as schematically shown in FIG. 1, shuttering is accomplished by a shutter 76 located between beam splitter 62 and photosensor 70 that is controlled by controller 24 to prevent or enable light 74 directed towards the photosensor by beam splitter 62 to propagate to the photosensor. In some embodiments, turning on and turning off the photosensor respectively accomplish shuttering the photosensor open and closed.

Following a predetermined delay from a time at which each light pulse 52 in the train of light pulses is radiated by light source 50 to illuminate person 22, controller 24 controls shutter 76 to shutter open photosensor 70 for a short exposure period. Light 74 that reaches 3D gaze tracker 20 during the exposure period is transmitted by shutter 76 and imaged onto photosensor 70 for registration by pixels 72 in the photosensor. An amount of light 74 registered by a given pixel 72 during the short exposure period is a portion of a total amount of light 74 reflected from the light pulse by a feature imaged on the pixel and directed towards photosensor 70 by beam splitter 62. The amount is a function of a distance of the feature from 3D gaze tracker 20.

The amounts of light reflected by features of person 22 from the light pulses in light pulse train 51 that are registered by pixels 72 provides a range image of the person. Controller 24 uses the amounts of light registered by the pixels to determine how long it takes light from light pulses 52 to travel round trip from light source 50 to the person's features respectively imaged on the pixels and back to 3D gaze tracker 20. The controller determines distances from the 3D gaze tracker of the features from the speed of light and the round trip times.

Light reflected by features of person 22 that is collected by optical lens 60 and not directed by beam splitter 62 to photosensor 70 is directed by the beam splitter to a photosensor 80, hereinafter referred to as a "picture photosensor 80", having pixels 82. A block arrow 84 schematically represents light directed by beam splitter 62 to picture photosensor 80, and the numeral 84 is used to reference the light. Optionally, a shutter 86 located between beam splitter 62 and picture photosensor 80 shutters the photosensor. Unlike range photosensor 70 however, picture photosensor 80 is shuttered open for relatively long exposure periods, sufficiently long so that substantially all the light reflected from a pulse 52 that is collected by 3D gaze tracker 20 and directed by beam splitter 62 to picture photosensor 80 (that is, light 84) is registered by the picture photosensor. Picture photosensor 80 therefore provides a contrast image 88, hereinafter also referred to as a "picture 88", of person 22, similar to conventional pictures acquired by a camera.

Whereas, generally a picture of person 22 imaged on picture photosensor 80 includes a picture of the person's head, and objects and possibly other people in the near vicinity of the person, for convenience of presentation, only eyes 100 of person 22 are shown in picture 88.

Controller 24 processes picture 88 using any of various pattern recognition algorithms to identify and locate an image of an eye 100 in the picture and identify at least one feature of the eye that is useable for determining a direction of gaze vector 42 associated with the eye. The at least one eye feature comprises at least one of the pupil, the iris, a boundary between the iris and the sclera, and a glint generated by light reflected off the eye. An enlarged image of eye 100 imaged by 3D gaze tracker 20 on picture photosensor 80 is schematically shown in an inset 110 in FIG. 1A. A glint 101, a pupil 102, an iris 103, sclera 104, and a boundary 105 between the sclera and iris are schematically shown for the eye in the inset. Controller 24 determines a direction of a gaze vector for the eye responsive to the at least one identified eye feature.

Figure 2A:
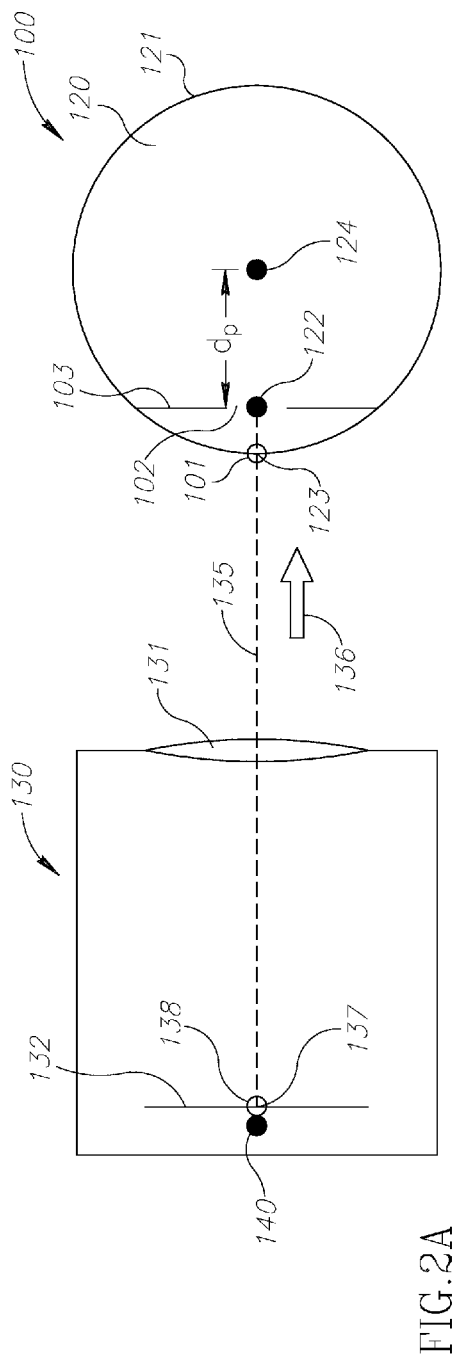
FIGS. 2A-2C schematically illustrate relationships between the pupil of an eye and a glint as a function of gaze angle that may be used by a 3D gaze tracker, in accordance with an embodiment of the invention.
Figure 2B:
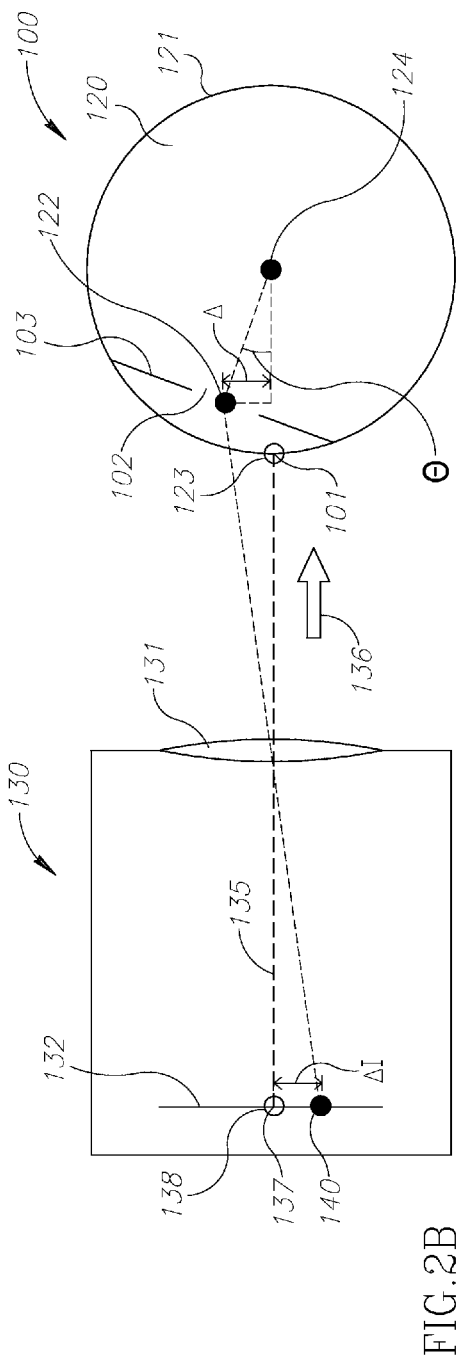
Figure 2C:
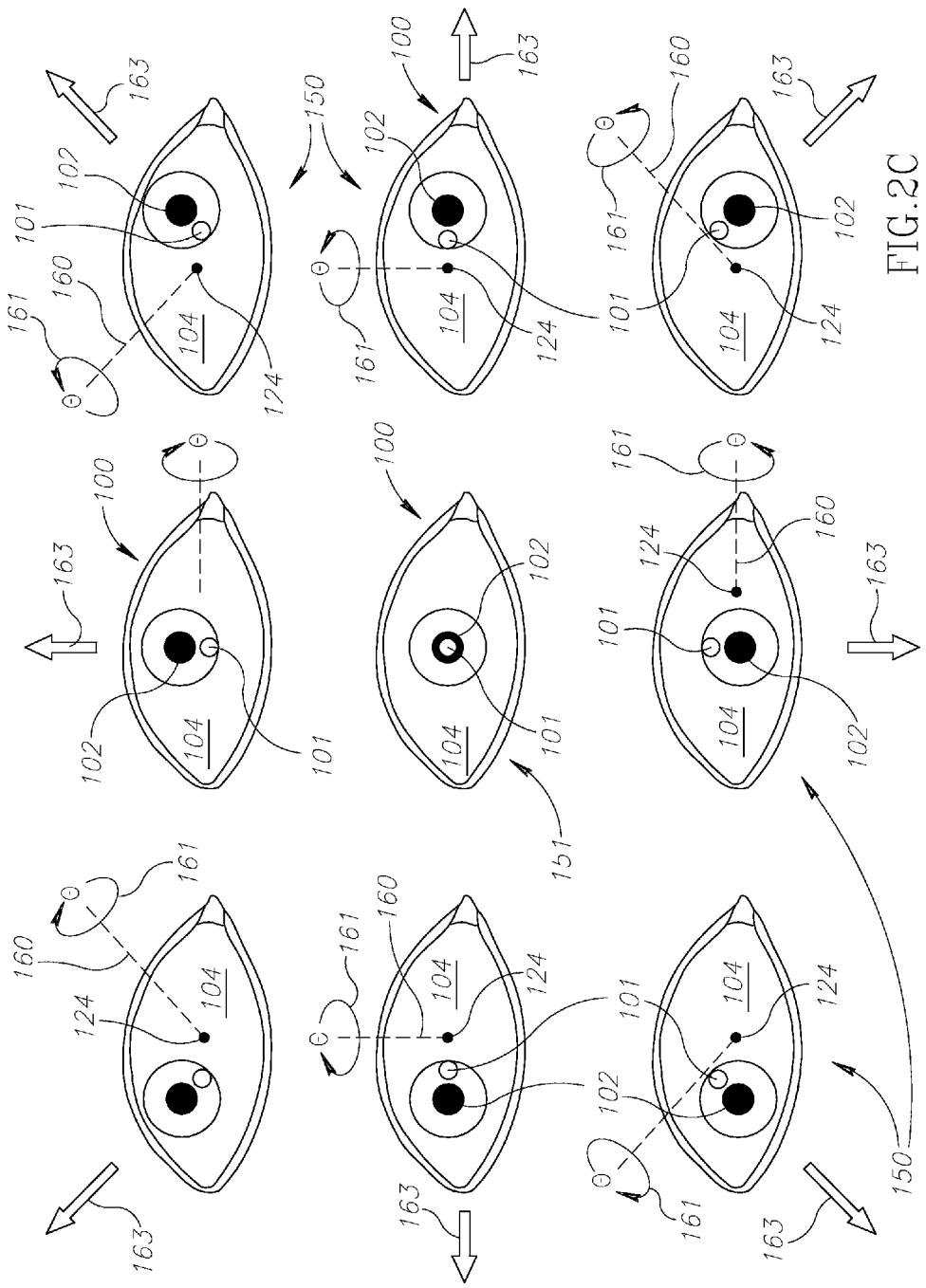

By way of example, in an embodiment of the invention, controller 24 determines gaze vector direction for an eye 100 of person 22 from locations of glint 101 and pupil 102 in the image of an eye 100 in picture 88. FIGS. 2A-2C schematically show relationships between features of eye 100 that may be used in an embodiment of the invention for determining gaze direction for person 22 responsive to images of glint 101 and pupil 102 of the eye.

FIGS. 2A and 2B show a schematic circular cross section 120 of an eye 100, assumed to be a sphere having a surface 121, center of rotation 124, an iris 103, and a pupil 102 having a center 122 located at a distance "$d_P$" from center of rotation 124. Whereas the eye is not a perfect sphere, but is slightly ovate with a bulge at the location of the cornea, modeling the eye as a sphere provides qualitative and quantitative insight into aspects of determining gaze direction. Typically, the eye has a diameter equal to about 24 mm (millimeters) and $d_P$ is equal to about 10 mm.

In FIGS. 2A and 2B a camera 130 comprising a lens 131 and a photosensor 132 is shown imaging eye 100. Functioning of camera 130 in imaging eye 100 simulates imaging of eyes 100 of person 22 by lens 60 (FIG. 1A) and picture photosensor 80 in 3D gaze tracker 20. Principles of the imaging that apply to camera 130 also apply to imaging of the eyes by 3D gaze tracker 20.

In FIG. 2A, center of rotation 124 of eye 100 is assumed by way of example to be located along an optical axis 135 of camera 130 and the eye is assumed to be illuminated by light, represented by a block arrow 136 that is coaxial with the optical axis. The light is reflected by surface 121 of eye 100 to generate a glint 101 at an intersection 123 of the optical axis and the eye surface. The glint is imaged on a photosensor 132 with a center of the glint image located at an intersection 137 of optical axis 135 and the photosensor. A circle 138 at intersection 137 schematically represents the image of glint 101.

In the figure, a gaze of eye 100 is assumed to be directed towards camera 130 along optical axis 135. As a result, pupil 102 is aligned with glint 101 and center 122 of the pupil lies on optical axis 135. Pupil 102 is imaged on photosensor 132 with the center of the pupil image located at intersection 137 and coincident with the center of image 138 of glint 101. The image of pupil 102 is schematically represented by a filled circle 140 located to the left of circle 138 representing the image of glint 101.

FIG. 2B schematically shows eye 100 being imaged as in FIG. 2A, but with the eye and its gaze direction rotated "upwards" by an angle θ. As a result, whereas glint 101 has not moved, pupil 102 is no longer aligned with glint 101 along optic axis 135. Center 122 of pupil 102 is located a distance $\Delta = d_P \sin\theta$ from optic axis 135 and image 140 of the center of pupil 102 is no longer located at intersection 137 and no longer coincident with the center of glint 101.

If magnification of camera 130 is represented by "M", centers of images 138 and 140 of glint 101 and pupil 102 are separated by a distance $\Delta_I = M\Delta = Md_P \sin\theta$. Gaze direction θ of eye 100 can be determined from a relationship $\sin\theta = (\Delta_I/Md_P)$. In practice, images of a pupil and a glint are generally not perfect circles, and typically $\Delta_I$ is determined as a distance between centroids of images of the pupil and the glint.

FIG. 2C shows schematic images 150 of eye 100, and in each image shows images of glint 101, pupil 102, iris 103 and sclera 104 for the eye, acquired by camera 130 (FIGS. 2A and 2B) for rotations of the eye by a same angle θ about different axes through center of rotation 124 of the eye. All the images are associated with a same position of center of rotation 124 along optical axis 135 (FIGS. 2A and 2B).

A central image 151 corresponds to an image acquired for eye 100 for the orientation of the eye shown in FIG. 2A, for which there is no rotation (θ=0) of the eye, and glint 101 is aligned with pupil 102 along optical axis 135. Each of the other eye images 150 is associated with an axis 160 of rotation about which the eye in the image and direction of gaze of the eye is rotated by same angle θ. The axis of rotation passes though the center of rotation 124 (FIGS. 2A and 2B) of the eye, is parallel to the plane of FIG. 2C, and is associated with a circle arrow 161 indicating direction of rotation of the eye about the axis. Direction of gaze for each image 150 of the eye relative to the gaze direction of central image 151 along optical axis 135 (FIGS. 2A and 2B), is schematically indicated by a block arrow 163. For each different rotation of eye 100 and its associated direction of gaze, orientation of glint 101 and pupil 102 is different, and the orientation and distance between the centers of the glint and pupil may be used to determine direction of gaze of person 22.

It is noted that embodiments of the invention, are not limited to determining gaze direction in accordance with the discussion above. For example, an embodiment may determine gaze direction of a person by processing images of his or her eyes to determine centers or centroids of their irises rather than centers or centroids of the pupils. The embodiment may use a location of the centers or centroids of the irises relative to a centroid or center of a glint to determine gaze direction. In some embodiments, direction of gaze of an eye is determined from a distribution in an image of the eye of regions determined to belong to the eye's sclera (referenced by numeral 104 in FIGS. 1, and 2C) relative to regions that are determined to belong to the iris. In some embodiments relative motion of Purkinje reflections, in particular the glint and the fourth Purkinje reflection, which is a reflection from the back of the eye lens, is used to determine direction of gaze.

FIGS. 2A-2C, and the above description of the Figs. provide a very simplified exposition of a method of determining gaze direction from images of glints and pupils. In practice, determining eye direction from images of pupils and glints generally comprises accounting for head motion, differences in the eye structure of different individuals, and, advantageously, calibrating images of eyes with eye gaze directions.

Figure 3A:
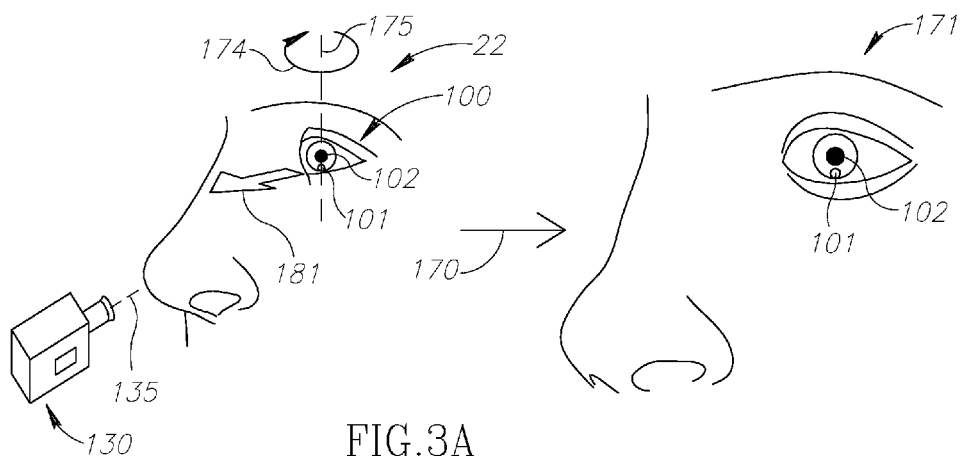
FIGS. 3A-3C schematically illustrate aspects of head orientation on determination of gaze direction.
Figure 3B:
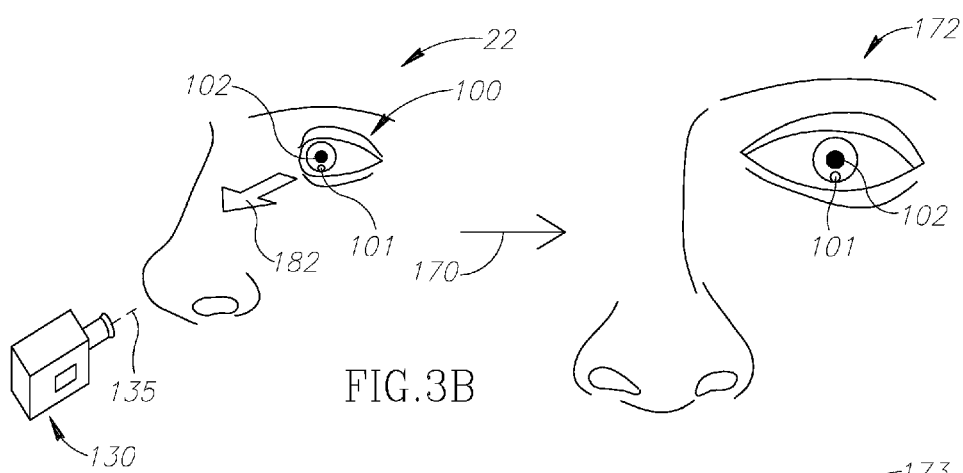
Figure 3C:
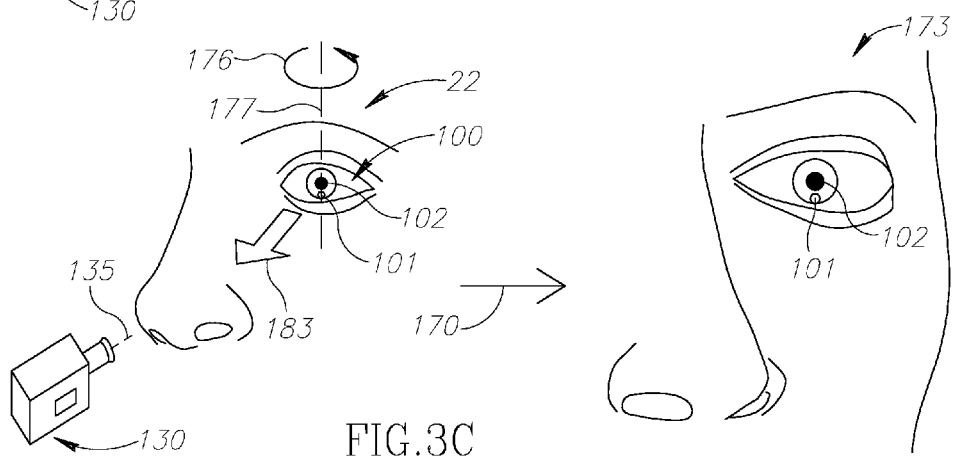

Influence of head orientation on gaze direction and limitations of determining gaze direction responsive only to relative positions of the pupil of an eye and the glint are illustrated for a simplified set of circumstances in FIG. 3A-FIG. 3C.

All the figures show, very schematically, on a left side of the figure, a perspective view of a camera 130 imaging a person 22 to acquire pictures of the person's eye 100 for determining his or her direction of gaze responsive to relative positions of a glint 101 and pupil 102 in the acquired pictures. An arrow 170 in FIGS. 3A, 3B and 3C points from the schematic perspective view in the figure to a schematic picture 171, 172, and 173 respectively, of the person acquired by camera 130.

In FIG. 3B, camera 130 is assumed to be directly in front of person 22, with its optic axis 135 aligned with and pointing at the person's nose. The person is looking slightly upward along a direction indicated by a block arrow 182. In picture 172 of the person acquired by camera 130, glint 101 is therefore directly below pupil 102. The relative positions of the glint and pupil indicate the alignment of the person with the camera and the slightly upward direction of the person's gaze.

In FIG. 3A the only change in the relative positions of camera 130 and person 22 is that the person's head is rotated clockwise in a direction indicated by a circle arrow 174, about an axis 175 that passes through the center of pupil 102 and the center of glint 101. As a result, the person is looking along a direction indicated by a block arrow 181 that is rotated with respect to the gaze direction indicated by block arrow 182 in FIG. 3B. However, whereas the gaze direction of the person in FIG. 3A is different from that in FIG. 3B, relative locations of pupil 102 and glint 101 in picture 171 of the person in FIG. 3A are the same as those in picture 172 of the person in FIG. 3B. The relative locations are the same because the head is rotated about an axis through the pupil and glint.

In FIG. 3C, the only change in the positions of camera 130 and person 22 relative to their positions in FIG. 3B is that the person's head is rotated counterclockwise in a direction indicated by a circle arrow 176 about axis 177 by an angle equal in magnitude, but opposite in direction to that of the rotation angle in FIG. 3A. A block arrow 183 indicates direction of gaze of person 22 in FIG. 3C. Whereas direction of gaze indicated by block arrow 183 is different from gaze directions indicated by block arrows 181 and 182, location of pupil 102 relative to glint 101 in picture 173 is the same as in pictures 171 and 172.

For the conditions noted in the discussion of FIGS. 3A-3C, the images of glint 101 and pupil 102 in FIGS. 171, 172 and 173 do not distinguish the gaze directions represented by block arrows 181, 182 and 183. Without additional information, such as orientation of the person's head in FIGS. 3A-3C, glint 101 and pupil 102 acquired by camera 130 by themselves do not disambiguate gaze directions indicated by the block arrows. Images of the person's features, for example images of direction of the nose, in pictures 171, 173 and 174 may provide additional information useable to determine a direction of the person's head and differentiate the gaze directions.

In an embodiment of the invention, controller 24 processes range images acquired by range photosensor 70 and/or pictures of person 22 shown in FIGS. 1A and 1B acquired by picture photosensor 80 to determine head orientation of person 22 for use in determining gaze directions of the person.

For example, in an embodiment of the invention, controller 24 processes range images of person 22 to determine distances from 3D gaze tracker 20 of features, hereinafter referred to as "fiducial features", of the person's head that may advantageously be used to indicate orientation of the head. Fiducial features may include facial features such as the forehead, eyes, tip of the nose, lips and chin, and the ears. Distances of the eyes, cheekbones, or ears of person 22 from the 3D gaze tracker may be used to determine an azimuthal angle of the person's head. An azimuthal angle is an angle about an axis through the person's head that is perpendicular to the ground when the person is standing upright with the head. A tilt angle of the head about an axis through the ears, which axis is parallel to the ground when the person is standing upright may be determined responsive to distance from 3D gaze tracker 20 of the person's forehead and chin.

In an embodiment of the invention, fiducial features are identified responsive to their images in a picture acquired by picture photosensor 80 (FIGS. 1A and 1B). Distances to the fiducial features imaged on pixels 82 in picture photosensor 80 are determined from distances provided by corresponding pixels 72 in range photosensor 70 on which light from the fiducial features is imaged.

To facilitate determining correspondence of pixels 72 in range photosensor 70 with pixels 82 in picture photosensor 80, optionally, the photosensors are configured having equal size pixels and are positioned and mounted in 3D gaze tracker 20 so that homologous pixels image same regions in FOV 30.

In some embodiments of the invention, pixels 72 and pixels 82 may have different sizes. For example, generally, intensity of light in light pulses 52 is limited by cost considerations and heat dissipation requirements for maintaining light source 50 (FIGS. 1A and 1B) and components of 3D gaze tracker 20 at acceptable operating temperatures. In addition, durations of the light pulses and exposure periods provided by shutter 76 are relatively short and may be less than 10 or 20 ns (nanoseconds). Amounts of light from light source 50 reflected by person 22 that are available per pixel 72 of range photosensor 70 for acquiring a range image of the person may therefore be limited. As a result, for pixels 72 in range photosensor 70 to register quantities of light sufficient to provide signals having acceptable signal to noise ratios (SNRs), it can be advantageous for the pixels to be relatively large. In an embodiment of the invention therefore, pixels 72, which are typically square, may advantageously have side dimensions greater than about 10μ (microns).

On the other hand, because exposure periods of picture photosensor 80 may be at least three times longer than exposure periods of range photosensor 70, more light is generally available for imaging a person on picture photosensor 80 than for imaging the person on range photosensor 70. To resolve distances between a glint and the pupil of an eye, pixels 82 in picture photosensor 80 are therefore advantageously relatively small.

In general, a maximum change in a distance between a glint and the pupil of an eye per degree of rotation of the eye is about 0.17 mm, if only the eye rotates and the glint is localized to the cornea. For example, for a 1° of change in angle θ of direction of a person's gaze, distance Δ in FIG. 2B relative to optical axis 135 in the figure changes by about 0.17 mm. If 3D gaze tracker 20 images person 22 at a magnification of about $10^{-2}$ on picture photosensor 80, to resolve changes of about 2° in θ responsive to changes in distance between pupil 102 and glint 101, pixels 72 in the picture photosensor are advantageously less than or equal to about 2.5μ on a side.

In some embodiments for which pixels 72 and 82 differ in size, range and picture photosensors 70 and 80 are aligned so that the larger pixels in one of the photosensors are substantially homologous with tiles of smaller pixels in the other of the photosensors and image same regions of FOV 30 that their homologous tiles image. For example, in an embodiment of the invention for which pixels 72 in range photosensor 70 are 10µ along a side and pixels 82 in picture photosensor 80 are 2.5µ along a side, large pixels 72 in range photosensor 70 may be homologous with square tiles comprising 16 small, 2.5µ pixels 82 in picture photosensor 80.

In some embodiments of the invention to accommodate different requirements and constraints of imaging on range photosensor 70 and picture photosensor 80, 3D gaze tracker 20 comprises optics for adjusting magnification of imaging on the photosensors independently of each other.

For example, an embodiment of the invention may comprise optical elements, such as zoom lens optics (not shown) located between beam splitter 62 and picture photosensor 80 that controller 24 controls to adjust magnification of images of person 22 formed on the picture photosensor. For situations in which person 22 is far from 3D gaze tracker 20, the controller optionally controls the zoom lens optics to zoom in on the person and magnify an image of eyes 100 and distances between glints 101 and pupils 102 in the image. The increased magnification improves accuracy with which distances between glints and pupils, and thereby gaze directions, are determined. In an embodiment of the invention, controller 24 controls magnification of images on picture photosensor 80 responsive to distances to person 22 provided by range images acquired by range photosensor 70, and increases and decreases magnification as images acquired by the range photosensor indicate increase and decrease respectively in distance of person 22 from 3D gaze tracker 20.

In some embodiments of the invention, controller 24 controls intensity of light in light pulses 52 responsive to distance measurements provided by range photosensor 70. As person 22 moves farther from or closer to 3D gaze tracker 20, the controller respectively increases and decreases intensity of light in light pulses 52. Adjusting light intensity as a function of distance can improve efficiency with which light from light source 50 is used. For constant intensity of light transmitted by light source 50, SNR of signals provided by pixels 72 for determining distance of features of person 22 is inversely proportional to the square of the distance of the person from 3D gaze tracker 20. Increasing illumination with distance can compensate, at least partially, for decrease in intensity of illumination of person 22 as the person moves away from 3D gaze tracker 20.

In some embodiments of the invention, light source 50 is controllable to direct light pulses 52 into a cone, hereinafter an "illumination cone", having a desired direction and solid angle to concentrate light in a limited region in FOV 30 and improve efficiency with which light form the light source is used to illuminate person 22. In an embodiment of the invention, controller 24 controls direction and solid angle of the cone responsive to location of the face and head of person 22 in FOV 30 determined from images acquired by range photosensor 70 and/or picture photosensor 80 to concentrate light on the person's face, or a portion thereof. By illuminating a limited region of FOV 30 that contains the head of person 22, or a portion of the head, such as a portion comprising the eyes, intensity of light available for imaging the head and/or eyes can be increased, and accuracy of gaze vector determination improved.

Figure 4:
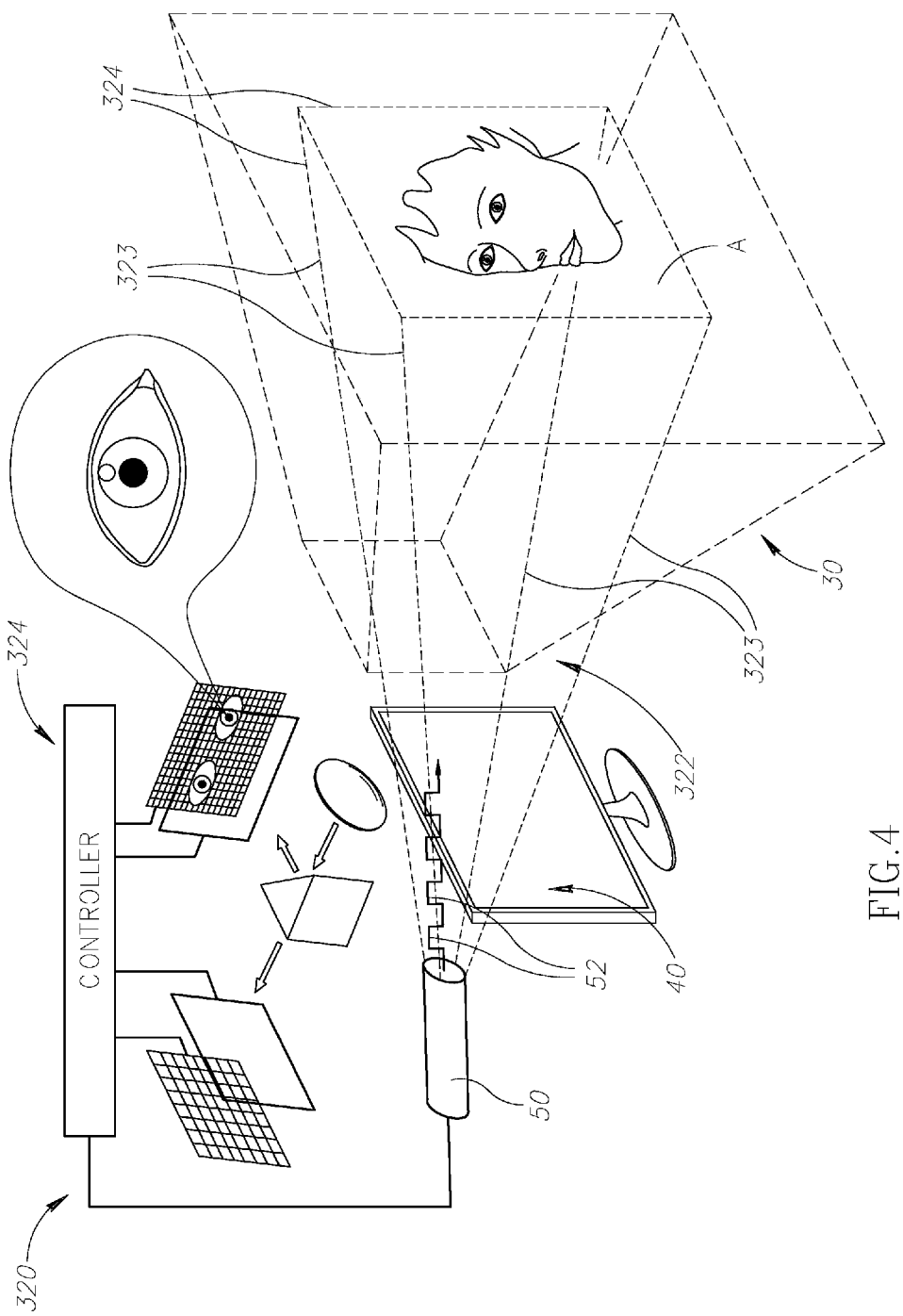
FIG. 4 schematically shows a 3D gaze tracker that concentrates light on a person's head to acquire range images and pictures for determining a gaze direction and POR for the person, in accordance with an embodiment of the invention.

FIG. 4 schematically shows a 3D gaze tracker 320 similar to 3D gaze tracker 20 shown in FIGS. 1A and 1B generating and directing an illumination cone 322, shown shaded, to concentrate light in a limited portion of FOV 30 to illuminate the head and face of a person 22, in accordance with an embodiment of the invention. A portion of illumination cone 322 is outlined by dashed lines 323 that extend from light source 50 to corners of an optionally square illumination area "A" outlined by dashed lines 324.

Area A is an area illuminated by light from light pulses 52 and is assumed to be located at a distance "D" of person 22 from 3D gaze tracker 320. Area A determines a solid angle, $\Omega$, of illumination cone 322 in accordance with an expression $\Omega = A/D^2$. A is optionally independent of D and optionally constant, for any distance of person 22 D within FOV 30. A is optionally determined so that in a time it takes 3D gaze tracker 320 to acquire an image of person 22, the person cannot generally move his or her head fast enough from a location along a central axis (not shown) of the illumination cone to move the head out of illumination cone 322.

Optionally, area A is a square area having a side length equal to about 50 cm. Assuming that images of person 22 are acquired by 3D gaze tracker 320 at a video rate of 30 images per second it requires about 30 ms (milliseconds) for the 3D gaze tracker to acquire an image. In 30 ms, a person moving at 10 km (kilometers) per hour moves about 10 cm. A 50 cm by 50 cm square illumination area A is therefore generally sufficient for defining a light cone that can be directed to track and provide continuous, advantageous illumination of a person moving in FOV 30.

Any of various devices and methods can be used in practice of an embodiment of the invention to generate and control direction and solid angle of illumination cone 322. For example, the light source may comprise an array of micro mirrors controllable to reflect and direct light provided by the light source into illumination cone 322. Optionally, the light source comprises a lens system, for example a zoom lens system having a focal point located at a light emitting element of the light source, for controlling the solid angle of illumination cone 322. In some embodiments of the invention, the light source comprises a mechanical system that rotates the light source to direct illumination cone 322 to maintain person 22 within the illumination cone. In some embodiments of the invention, different light sources are turned on and off to maintain person 22 within a small angle illumination cone as the person moves around in FOV 30.

Except for the rare and generally uninteresting circumstance for which a person looks directly at a camera that is imaging the person, gaze direction by itself is not sufficient to define a gaze vector for the person and determine therefrom a POR. For most circumstances, three spatial coordinates (for example, x, y, and z coordinates of a Cartesian coordinate system) of an origin for the gaze vector is required to locate the gaze vector in space and determine a POR for the gaze vector.

In an embodiment of the invention, range images of a person, such as person 22 in FOV 30 of 3D gaze tracker 20 (FIG. 1A), acquired by range photosensor 70 and/or pictures of the person provided by picture photosensor 80 are processed by controller 24 to provide 3D spatial coordinates for origins of the person's gaze vectors. In particular, distances from 3D gaze tracker 20 determined responsive to range images acquired by range photosensor 70 are used to provide a z-coordinate for the origins. A z-coordinate is arbitrarily assumed to be a coordinate measured along a z-axis of an x,y,z, Cartesian coordinate system for which the z-axis is parallel to optical axis 61 (FIGS. 1A and 1B) of 3D gaze tracker 20.

Whereas three spatial coordinates for a person's eye can usually be estimated from an image analysis of a picture of the person acquired by a camera, such estimates are generally practical for a limited range of distances from the camera, and are typically associated with relatively large margins of error. A TOF 3D camera, such as provided by range photosensor 70 and associated optics in 3D gaze tracker 20, can provide spatial coordinates, and in particular a coordinate for distance from the 3D camera and therefore a z-coordinate of the eye relative to the camera, having a relatively small margin for error.

Figure 5:
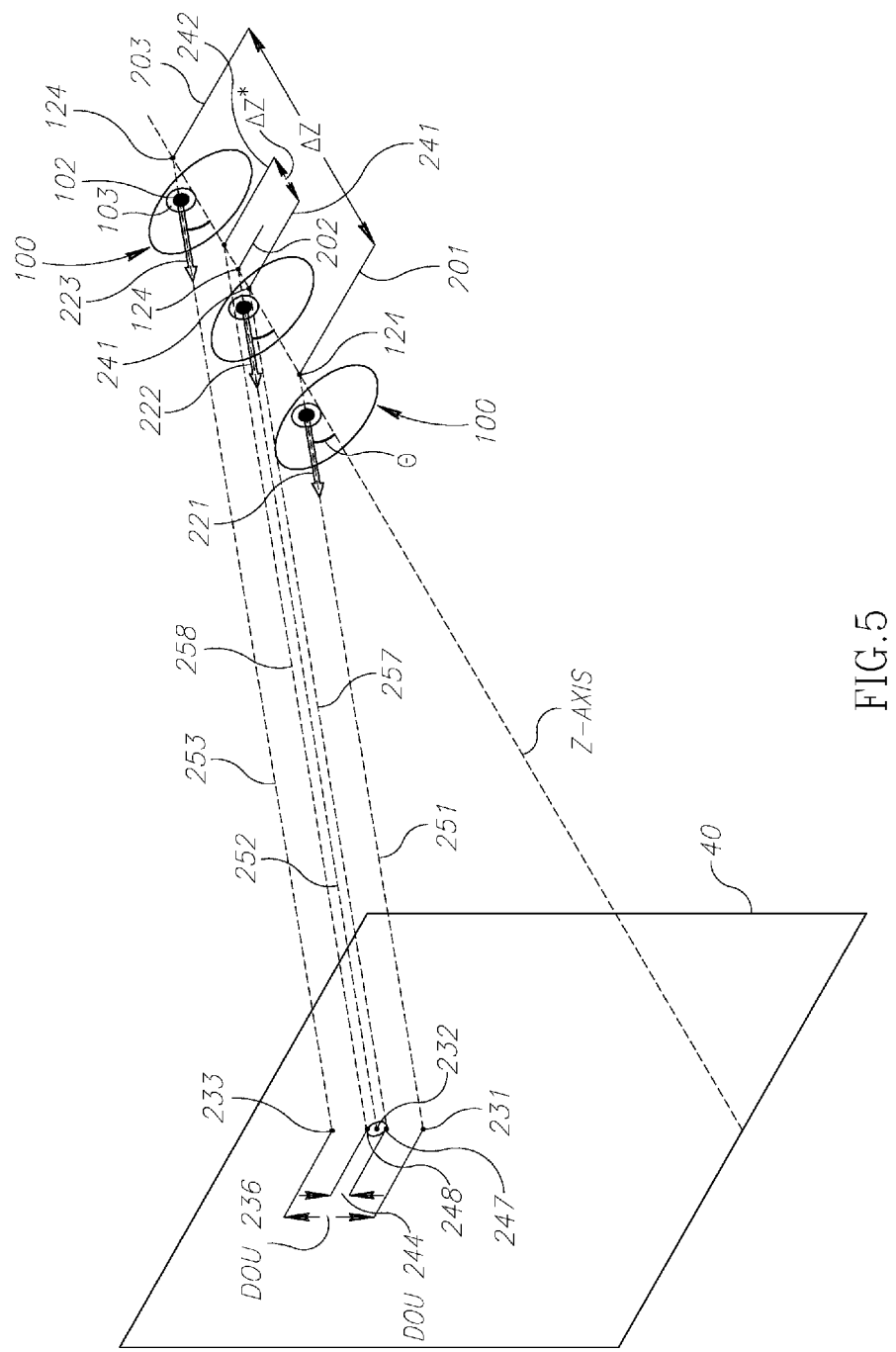
FIG. 5 schematically illustrates aspects of determining an origin for a gaze vector of an eye and its associated POR responsive to distance of the eye from a gaze tracker, in accordance with an embodiment of the invention.
Figure 6:
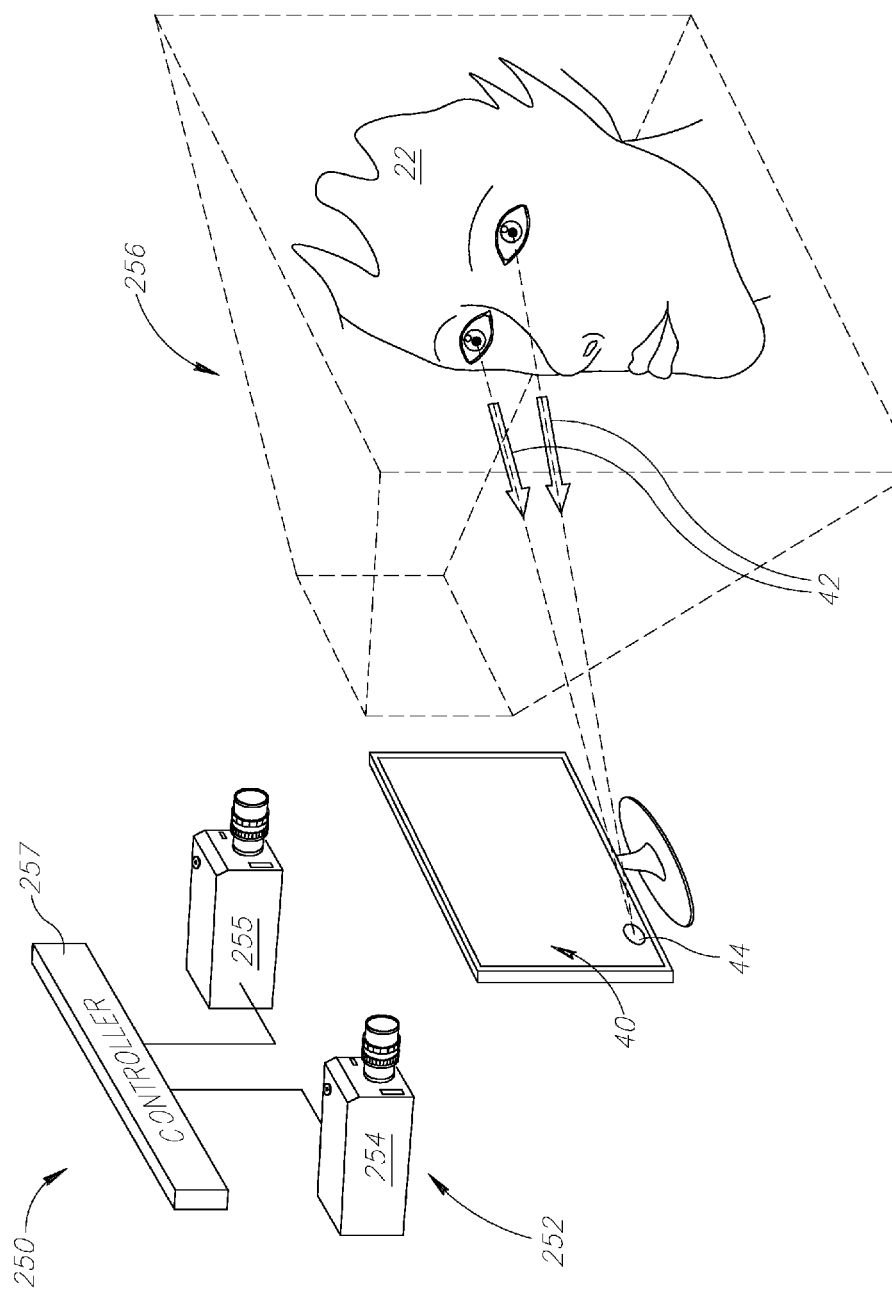
FIG. 6 schematically shows a 3D gaze tracker comprising a stereoscopic 3D camera determining gaze vectors and a POR for a person in accordance with an embodiment of the invention.

FIG. 5 schematically shows a very simplified configuration that illustrates how uncertainty in determining distance of a person's eye from a camera (not shown) that images the person generates uncertainty in identifying a POR for the person from a gaze vector determined for the eye. The figure shows an eye, schematically represented by an ellipse 100, at three different collinear positions at different distances, indicated by witness lines 201, 202, and 203, from a video display 40. The positions are arbitrarily defined to be the positions of the centers of rotation 124 of the eye and are located along a same line, referred to as a "z-axis", perpendicular to the video display. The positions indicated by the witness lines are referred to by the numerals 201, 202, and 203 labeling the witness lines, and the eye is referred to by the numeral 100 labeling the ellipse representing the eye. Distance of the eye from the camera imaging the eye is assumed to be the same as distance of the eye from video display 40.

At each position 201, 202 and 203, the eye has a gaze vector 221, 222, and 223 respectively. Each gaze vector 221, 222, and 223 extends along a dashed line 251, 252, and 253 respectively that passes from the eye's center of rotation 124 through the center of its pupil 102. All the gaze vectors make a same inclination angle $\theta$ with the z-axis. Gaze vectors 221, 222, and 223 intersect video screen 40 at intersection points 231, 232, and 233 respectively, where dashed line 251, 252, and 253 associated with the gaze vectors intersect the video screen. Intersections 231, 232, and 233 represent locations of PORs on video display 40 that are determined from gaze vectors 221, 222, and 223 respectively.

The eye is assumed to actually be located at "middle" position 202, and intersection 232 an actual POR for gaze vector 222 associated with the eye at the middle position. Positions 201 and 203 represent lower and upper bound estimates respectively for the z-coordinate of the eye that might reasonably result from image analysis of a picture that images the eye. A distance "$\Delta Z$" between positions 201 and 203 represents an uncertainty in the z-coordinate of the eye determined from the image analysis. A concomitant uncertainty in where the actual POR is located, is represented by a "distance of uncertainty (DOU)" 236, between intersection points 231 and 233 on video display 40.

Z-coordinates indicated by witness lines 241 and 242 along the z-axis are referred to by numerals 241 and 242 and represent reasonable lower and upper error bounds respectively in the z-coordinate of the eye determined by a TOF 3D camera. By way of example, witness lines 241 and 242 may represent z-coordinate lower and upper error bounds, respectively, for the TOF 3D camera comprising light source 50, range photosensor 70 and associated optical elements in 3D gaze tracker 20. Distance "$\Delta Z^*$" between z-coordinates 241 and 242 represents an uncertainty in a z-coordinate for the eye determined by the TOF camera.

If eye 100 were located at 241, it is assumed that its gaze vector (not shown) would lie along a dashed line 257 that extends from point 241 at an angle $\theta$ with respect to the z-axis. The eye would be determined to have a POR located at an intersection point 247 of dashed line 257 with video screen 40. Similarly, if eye 100 were located at position 242, it would be determined to have a POR located at an intersection point 248 of a dashed line 258 with video screen 40. The uncertainty generates a corresponding DOU 244, which is a distance between intersection points 247 and 248. DOU 244 provided by the TOF 3D camera is generally smaller than DOU 236 provided by image analysis alone.

By way of numerical example, assume that a person's eye 100 is located at a distance of about 50 cm from video display 40 and that the video display has a diagonal dimension of about 60 cm so that a gaze angle $\theta$ for the eye may often be as large as 30°. An uncertainty $\Delta Z$ in a z-coordinate for the person's eye provided by image analysis may reasonably be assumed to be about 5 cm (±2.5 cm). The uncertainty results in an uncertainty, DOU 236, in the location of a POR for the eye that may be estimated by the expression DOU 236=$\Delta Z$ tan $\theta$, which for $\Delta Z$=5 cm and $\theta$=30°, is equal to about 3 cm.

On the other hand, an uncertainty in the z-coordinate for the eye determined by a TOF 3D camera may reasonably be assumed equal to about 1 cm (±0.5 cm) resulting in an uncertainty DOU 244 in the location of the POR for $\theta$=30° equal to about 0.6 cm. For example, assume a TOF 3D camera that illuminates a FOV having a view angle of 45° with light pulses having intensity greater than or equal to about 50 milliwatts and pulse width between 15 and 20 ns that images objects in the FOV on a photosensor comprising 10µ×10µ pixels. The camera can generally provide distance measurements characterized by z-coordinate accuracy equal to about 1 cm for distance measurements between about 0.5 m and 3 m.

In an embodiment of the invention, to calibrate 3D gaze tracker 20 shown in FIGS. 1A and 1B (or 3D gaze tracker 320 FIG. 4), and adapt the 3D gaze tracker to differences in eye structure and facial features of different users of the 3D gaze tracker, the 3D gaze tracker and display on video display 40 are controlled to acquire calibration images of the users.

In an embodiment, acquiring calibration images for a user, such as person 22 shown in FIGS. 1A and 1B, comprises imaging the person for each of a plurality of different "calibration positions" in FOV 30. Different calibration positions differ in distance from gaze tracker 20 and/or location in FOV 30. For each calibration position, a range image and a picture of the person are acquired for each of a plurality of different "calibration PORs" presented on video display 40 to which the person's gaze is directed. Optionally, for a plurality of calibration positions, the person is requested to maintain his or her head in a fixed position and move only the eyes to direct gaze at different calibration PORs.

The images are processed to provide 3D spatial coordinates for the person's eye features, such as the pupil, iris, sclera, glints or Purkinje reflections, and/or fiducial features, for each of the calibration positions and calibration PORs. The gaze vector for a given calibration position and POR is optionally determined by 3D spatial coordinates of the given calibration position and location of the calibration POR on video screen 40. The eye feature and fiducial feature coordinates, and associated gaze vectors, are stored as reference data in a suitable data array. In an embodiment of the invention, the reference data array is used to determine gaze vectors of person 22 as the person moves around freely in FOV 30.

In some embodiments of the invention, to determine a gaze vector for person 22 at a given time and position in FOV 30, responsive to values in the reference data array, 3D gaze tracker 20 acquires a range image and picture of the person at the given time and position. Controller 24 processes the range image and picture to identify and determine spatial coordinates for eye and fiducial features of the person.

To determine head orientation of the person, the controller optionally determines an affine transformation of reference coordinates of fiducial features that, in accordance with a best fit criterion, such as a least squares criterion, most closely reproduces the 3D spatial coordinates determined for the fiducial features. A transformation of a head orientation associated with the reference coordinates by the affine transformation provides the head orientation. A gaze vector direction relative to the head orientation of the person is determined responsive to coordinates of the eye features. The head orientation, gaze vector direction, and a gaze vector origin, optionally determined from spatial coordinates of the eye, define the gaze vector.

In some embodiments of the invention, controller 24 interpolates reference data values responsive to spatial coordinates for eye and fiducial features of the person provided from the range image and picture to determine a gaze vector for person 22.

In the above discussion, 3D gaze trackers are shown comprising a TOF 3D camera, which though sharing optical components with a picture camera is separate from the picture camera. Embodiments of the invention are not however, limited to 3D gaze trackers having separate range and picture cameras, nor to TOF 3D cameras.

In some embodiments of the invention, a 3D gaze tracker comprises a single photosensor, which is used to acquire both range images of a person and pictures of the person. A shutter that shutters the photosensor is controlled to shutter the photosensor open for exposure periods to acquire range images of the person that have durations, which are different from durations of exposure periods that the shutter provides for acquiring pictures of the person.

And in some embodiments of the invention, a 3D gaze tracker comprises a stereoscopic 3D imager that determines distances to features of a person in the 3D gaze tracker's FOV responsive to parallax exhibited by images of the features provided by two, spatially separated cameras in the system.

FIG. 6 schematically shows a stereoscopic 3D gaze tracker 250 comprising a stereoscopic 3D imager 252 having two spatially separated cameras 254 and 255 that acquire pictures (contrast images) of features in a FOV 256 of the 3D gaze tracker from different perspectives. A controller 257 in the stereoscopic 3D gaze tracker processes the pictures to identify and locate eye and fiducial features and determine spatial coordinates to the features responsive to distances to the features determined from parallax that they exhibit in the pictures.

It is noted that whereas in the above description, a 3D gaze tracker in accordance with an embodiment of the invention is used to interface a person with a computer that interacts with the person via a video display. However, embodiments of the invention are not limited to computers and systems that interface with a person via a video screen. For example, a smart "computerized" vending machine may comprise a 3D gaze tracker in accordance with an embodiment of the invention to determine which of a plurality of items the vending machine offers for sale a person wishes to buy. The 3D gaze tracker determines on which of the vending machine products the person's POR settles and in response the vending machine illuminates, for example, with an internal light source, the product to provide feedback to the person as to where the vending machine "thinks" the POR is located. If the POR remains substantially fixed on the product for a sufficient time after it is illuminated, the vending machine dispenses the product after payment from the person is received.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A system for interfacing a person with a computer, the system comprising:
   a video display on which the computer is operable to generate an image to interact with the person;
   a 3D camera to acquire a range image of the person located in a field of View (FOV) of the camera;
   a picture camera to acquire a picture of the person in the FOV of the 3D camera; and
   a controller to process the range image and the picture to determine spatial coordinates for features of the person's head and an eye of the person, to determine a gaze direction and origin for a gaze vector of the eye responsive to the determined spatial coordinates and to modify the image displayed on the video display responsive to the gaze vector.

2. A system according to claim 1 wherein modifying the displayed image comprises determining a point of regard (POR) responsive to the gaze vector and modifying the displayed image responsive to the POR.

3. A system according to claim 2 wherein modifying the displayed image responsive to the POR comprises generating an icon on the video display that indicates a location of the POR in the display.

4. A system according to claim 3 wherein the icon is configured to indicate a region of uncertainty (ROU) for the POR.

5. A system according to claim 1, wherein the FOV extends from a distance from the gaze tracker equal to about 0.3 m.

6. A system according to claim 1, wherein the FOV extends to a distance from the gaze tracker equal to or greater than about 2 m.

7. A system according to claim 1 and comprising a light source to illuminate at least a portion of the FOV.

8. A system according to claim 7 wherein the controller is operable to adjust intensity of light provided by the light source responsive to a spatial coordinate of the spatial coordinates determined by the controller.

9. A system according to claim 7 wherein the controller is operable to adjust direction of light provided by the light source responsive to a spatial coordinate of the spatial coordinates determined by the controller.

10. A system according to claim 1, wherein the features comprise at least one feature of the person's eye for which spatial coordinates can be used to determine gaze direction of the eye.

11. A system according to claim 1, wherein the features comprise at least one feature of the person's head for which spatial coordinates can be used to determine orientation of the head.

12. A system according to claim 1, wherein the 3D camera comprises a stereoscopic camera.

13. A system according to claim 1, wherein the 3D camera comprises a time of flight (TOF) 3D camera.

14. A system according to claim 1, wherein the displayed image is associated with a video game.

15. A system according to claim 14 the video game is an online video game.

16. A system for interfacing a person with a video game, the system comprising:
- a video display to display images associated with the video game;
- a 3D camera to acquire a range image of the person located in a field of view (FOV) of the camera;
- a picture camera to acquire a picture of the person in the FOV of the 3D camera; and
- a controller operable to process the range image and the picture to determine spatial coordinates for features of the person's head and an eye of the person, to determine a gaze direction and origin for a gaze vector of the eye responsive to the determined spatial coordinates and to modify the image displayed on the video display responsive to the gaze vector.

17. A system according to claim 16 wherein modifying the displayed images responsive to the POR comprises generating an icon on the video display that indicates a location of the POR in the display.

18. A system according to claim 16, wherein the features comprise at least one feature of the person's eye for which spatial coordinates can be used to determine gaze direction of the eye.

19. A system according to claim 16, wherein the features comprise at least one feature of the person's head for which spatial coordinates can be used to determine orientation of the head.

20. A method of interfacing a person with a computer the method comprising:
- acquiring a range image of a person that provides distances to the person's features;
- acquiring a contrast image of the person;
- processing the range and contrast images to provide a gaze vector for the person;
- providing the computer with information related to the gaze vector; and
- indicating to the person a point of regard determined responsive to the gaze vector.

* * * * *